United States Patent
Deininger et al.

(10) Patent No.: US 6,443,886 B2
(45) Date of Patent: Sep. 3, 2002

(54) VALVE AND METHODS FOR URINARY CONTROL

(75) Inventors: Steven T. Deininger, Edina; Richard M. Johnson, Minnetonka, both of MN (US)

(73) Assignee: American Medical Systems Inc., Minnetonka, MN (US)

(*) Notice: Subject to any disclaimer, the term of this patent is extended or adjusted under 35 U.S.C. 154(b) by 0 days.

(21) Appl. No.: 09/767,208

(22) Filed: Jan. 22, 2001

Related U.S. Application Data (63) Continuation of application No. 09/034,250, filed on Mar. 4, 1998, now Pat. No. 6,200,261.

(51) Int. Cl.[7] .................................................. A61F 2/00
(52) U.S. Cl. ................................................................ 600/29
(58) Field of Search ................... 600/29–32; 128/885; 251/342, 349, 353; 137/219, 843–844, 852

(56) References Cited

U.S. PATENT DOCUMENTS

| | | | |
|---|---|---|---|
| 2,510,766 A | 6/1950 | Surface | |
| 3,547,401 A | 12/1970 | Gurnee et al. | |
| 3,758,073 A | * 9/1973 | Schulte | 128/DIG. 25 |
| 3,841,304 A | 10/1974 | Jones | |
| 4,056,116 A | * 11/1977 | Carter et al. | 137/68.3 |
| 4,198,029 A | * 4/1980 | Johnson | 137/219 |
| 4,210,132 A | 7/1980 | Perlin | |
| 4,344,434 A | 8/1982 | Robertson | |
| 4,471,807 A | * 9/1984 | Lucking et al. | 137/614.12 |
| 4,552,128 A | 11/1985 | Haber | |
| 4,587,954 A | 5/1986 | Haber | |
| 4,631,062 A | 12/1986 | Lassen et al. | |
| 4,690,677 A | 9/1987 | Erb | |
| 4,691,836 A | 9/1987 | Wassilieff | |
| 4,822,333 A | 4/1989 | Lavarenne | |
| 4,968,294 A | 11/1990 | Salama | |
| 5,074,855 A | 12/1991 | Rosenbluth et al. | |
| 5,082,006 A | 1/1992 | Jonasson | |
| 5,114,398 A | 5/1992 | Trick et al. | |
| 5,813,973 A | * 9/1998 | Gloth | 600/29 |
| 6,200,261 B1 | 3/2001 | Deininger et al. | |

FOREIGN PATENT DOCUMENTS

| | | |
|---|---|---|
| DE | 520759 | 3/1931 |
| EP | 0535778 B1 | 7/1995 |
| EP | 780105 | 6/1997 |
| GB | 2267579 | 8/1993 |
| WO | 92/06731 | 4/1992 |
| WO | 92/11826 | 7/1992 |
| WO | 92/19192 | 11/1992 |
| WO | 93/08765 | 5/1993 |
| WO | 94/26215 | 11/1994 |
| WO | 96/26688 | 9/1996 |
| WO | 96/39096 | 12/1996 |
| WO | 9639989 | 12/1996 |
| WO | 9639990 | 12/1996 |
| WO | 9639991 | 12/1996 |
| WO | 97/06758 | 2/1997 |
| WO | 97/17909 | 5/1997 |
| WO | 97/25947 | 7/1997 |
| WO | 98/19640 | 5/1998 |
| WO | 98/25555 | 6/1998 |

* cited by examiner

*Primary Examiner*—Eric F. Winakur
*Assistant Examiner*—Joseph A. Cadugan
(74) *Attorney, Agent, or Firm*—Jeffrey J. Hohenshell (57) ABSTRACT

A valve movable between open and closed positions is described. The valve preferably has an integral hinge and includes an inherent bias toward the closed position. The valve is particularly suitable as a component of an article for treating urinary incontinence.

17 Claims, 7 Drawing Sheets

VALVE AND METHODS FOR URINARY CONTROL

RELATED APPLICATIONS

This application is a continuation of U.S. patent application Ser. No. 09/034,250, filed Mar. 4, 1998 now U.S. Pat. No. 6,200,261, which is incorporated herein by reference.

FIELD OF INVENTION

This invention relates to a valve for alleviating urinary incontinence. More particularly, the invention is concerned with a patient controlled valve to permit urination and prevent undesirable leakage of urine while allowing relief when needed without removal of the valve from the body of the patient. A most preferred embodiment of the device is for alleviating urinary incontinence, particularly stress incontinence, in a female patient.

BACKGROUND OF THE INVENTION

Urinary incontinence, which is a condition involving involuntary loss of urine, is a problem with many patients, particularly females, throughout the world. Sometimes the problem is treated with surgery or incontinence pads. Some patients can not receive surgery or suffers only from a partial loss of urine. Those problems may be treated non-surgically by use of internal (intra-urethral or intra-vaginal) or external devices. A number of external female devices have been patented.

For example, U.S. Pat. No. 5,074,855 discloses a device for controlling urinary incontinence in a human female including a resilient pad configured to seal against and occlude the urethral meatus of the user. A similar device is disclosed in U.S. Pat. No. 5,336,208. In those devices, an adhesive is provided to seal the body of the device against the urethral meatus.

International Applications No. 96139989, 96/39990 and 96/39991 each disclose a female urinary incontinence device in the form of an urethral cap with a partially deformable body portion, a hand gripping portion and a body contacting surface. The body portion defines a chamber which allows for a vacuum seal when applied to the patient's body.

Each of the above devices prevents urinary leakage by occluding the external urethral orifice and each has to be removed by the patient to allow micturition.

It is desirable to have a device which satisfactorily prevents leakage and also facilitates relief without the need to remove the device from the body of the patient. It has now been found that these benefits may be achieved with an easily operable valve which prevents leakage when closed and allows flow when open.

SUMMARY OF THE INVENTION

A valve adapted for closing a body orifice most preferably has a bulbous tube formed of a flexible material as its main structure and shape. The bulbous tube may have an inlet fixed across the body orifice and an outlet positioned away from the body orifice for controlling incontinence. A flange located around the inlet of the bulbous tube is used in the preferred embodiment to attach to the body. The flange most preferably has a generally flat ring shaped configuration to circumscribe the inlet and to interface about the body orifice. A passage is formed within and passes through the bulbous tube for extending from the inlet along an axis therethrough between the inlet and outlet. A wall of the bulbous tube is preferably integral therewith. The wall may be located between the inlet and the outlet. Consistent with the configuration the wall may have a barrel shape tapering toward the inlet and the outlet so the bulbous tube is most preferably wider therebetween. The wall can be between an inside and an outside.

A hinge is preferably part of the wall and about the bulbous tube. The hinge might be located in the wall substantially wherein the barrel shape wall defines the passage therethrough. The hinge may exist as an area of preferential bending so the bulbous tube is either normally barrel shaped or flipped with the outlet thereof folded about the hinge and into the passage. While the preferred hinge is, that is either open or closed, the hinge can also be arranged to be normally closed such that to keep it open the outlet must be pulled away from the seat by the user or the pressure of urination force from the bladder down the urethra holding the outlet away from the seat. This can be considered a monostable arrangement for the hinge but the valve would look the same since the bias of the hinge is not really apparent in illustrations.

A seat is preferably positioned within the bulbous tube. The seat can be in the preferred embodiment located on the inside of the wall. The seat may perhaps be disposed within the passage to engage the outlet when the bulbous tube is flipped into the passage after bending the hinge acutely. The outlet is most preferably then moved along the axis toward the inlet so the outlet may be held against the seat to seal the inlet and close the passage.

One or more holes are preferably dispose through the wall. Each hole might be located in a plane substantially normal to the axis and away from the inlet and axially beyond the hinge. The outlet may surround a bottom of the bulbous tube so that when the -flipped bulbous tube moves the bottom axially into the passage, the bottom locates the one or more holes dispose through the wall in contact with the seat and positions the bottom to close the inlet.

The outlet in an alternate embodiment most preferably includes a plug supported from the wall and within the outlet by a web so that when the flipped bulbous tube moves the plug axially through the passage. In that alternate configuration the plug contacts the seat and closes the inlet.

The wall about the inlet may in this version includes a pipe depending therefrom and into the passage so the seat is most preferably on the pipe away from the inlet. The seat on the pipe can be adapted to engage the plug for remotely closing the inlet. The inlet might include a duct positioned thereabout to surround the inlet and extend the passage away from the outlet, the duct, the flange and the bulbous tube are thus in this arrangement adapted for fluid communication with the body orifice.

The bulbous tube is preferred to be circular in cross section and substantially symmetrical about the axis and the inlet and outlet are substantially normal to the axis but need not be symmetric or circular. The bulbous tube could be formed of a flexible polymer by for example molding or casting. The outlet most preferably includes a grip projecting therefrom for use in pulling the outlet to flip the hinge and open the passage between the inlet and outlet.

A method of making a valve adapted for closing an orifice may include steps. Forming a bulbous tube of a flexible material may be a step. The step of having on the bulbous tube an inlet fixed for placement across the orifice and an outlet positioned away from the orifice is a step. The step of locating a flange with a generally flat ring shape around the inlet of the bulbous tube to interface about the orifice is preferably performed. Extending a passage within the bulbous tube from the inlet along an axis therethrough may be a preferred step. It is most preferred that having a barrel shaped wall on the bulbous tube with the wall tapering toward the inlet and the outlet and thus wider therebetween is a step. The wall between an inside and an outside.

Locating a hinge about the bulbous tube and in the wall as an area of preferential bending so the bulbous tube is either normally barrel shaped or flipped with the outlet folded about the hinge into the passage may be a step. The step of locating a seat on the inside of the wall to engage the outlet when the bulbous tube is flipped into the passage by bending the hinge acutely so the outlet is moved along the axis toward the inlet and held against the seat is in the method.

A method of using a valve may include the bulbous tube formed of a flexible material. The bulbous tube preferably has an inlet fixed across the orifice and an outlet opposite thereto. The bulbous tube has a barrel shape tapering toward the inlet and the outlet so the hinge about the bulbous tube. The hinge is an area of preferential bending so the bulbous tube is either normally barrel shaped or flipped with the outlet folded about the hinge. A seat within the bulbous tube seals the outlet. The method of using with the steps of flipping the bulbous tube by bending the hinge acutely so the outlet is moved toward the inlet and held against the seat. The method of using with the step of unfolding the acutely bent hinge. The method of using with the step of unfolding the acutely bent hinge by pressurizing the seat at the inlet but within the bulbous tube to unseal the outlet. The method of using with the step of unfolding the acutely bent hinge by pressing about the hinge to flip the outlet away from the seat.

DETAILED DESCRIPTION OF THE DRAWINGS

A valve 10 adapted for closing a body orifice (not shown) has a bulbous tube 11 formed of a flexible material as its main structure and shape. The bulbous tube 11 is preferably molded as one integral component but can be cast integrally or assembled from separately made parts, see FIGS. 1, 2, 3, 4, 5, 6, and 7. The bulbous tube 11 has an inlet 12 that is fixed across the body orifice and an outlet 13 positioned away from the body orifice for controlling incontinence. The outlet 13 is open when the valve 10 is unseated as will be understood upon a complete reading of this disclosure. The body orifice may be the female meatus and its passageway, the urethra, for urine (not shown in the FIGS.). A flange 14 located around the inlet 12 of the bulbous tube 11 is used in the preferred embodiment to attach to the body with a medical grade adhesive such as a moisture effusing acrylic. Skilled artisans would know the proper adhesive to accommodate bodily fluids without disconnection or leakage and to minimize irritation. The flange 14 most preferably has a generally flat ring shaped configuration to circumscribe the inlet 12 and to interface about the body orifice see FIGS. 1, 2, 3, 4, 5, 6 and 7.

Figure 1:
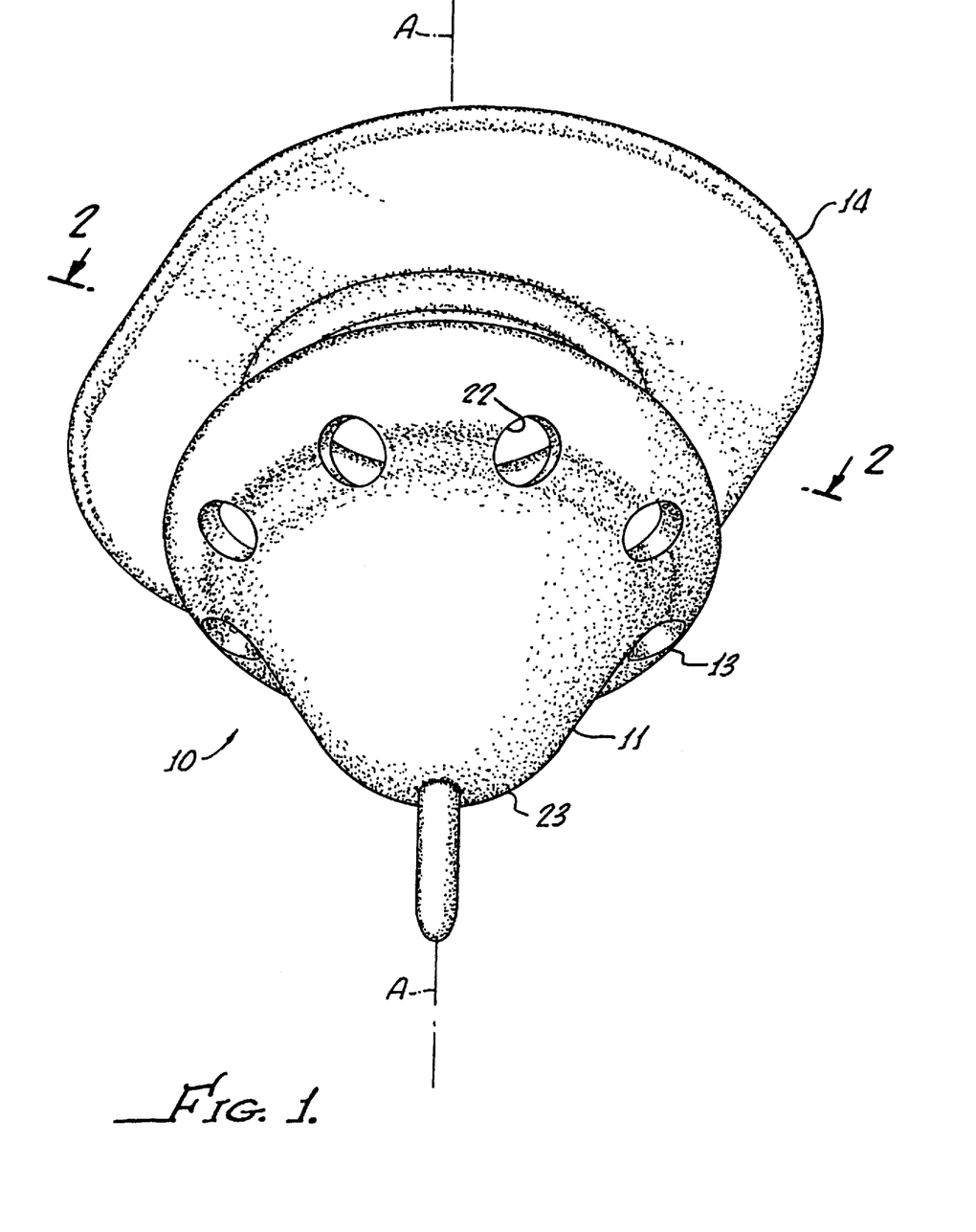
FIG. 1 is a view in perspective of the valve adapted for closing a body orifice (not shown) wherein the valve is shown in its open position.
Figures 2, 3:
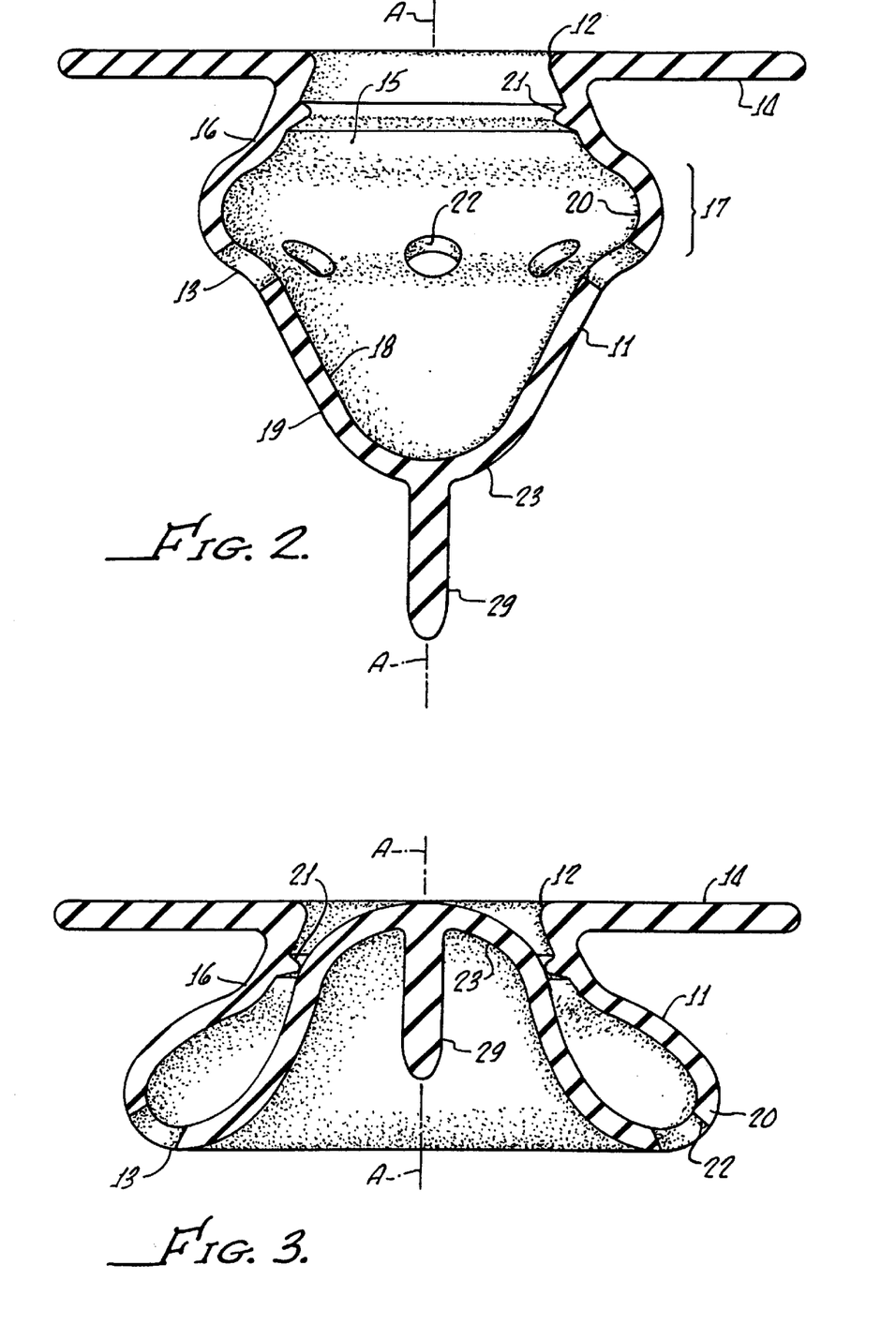
FIG. 2 is a view in cross section of the valve as would be seen along line 2—2 of FIG. 1.
FIG. 3 is a view in cross section of the valve similar to that of FIG. 2 but wherein therein the valve is shown flipped over center with respect to the hinge in its valve closed position.
Figure 5:
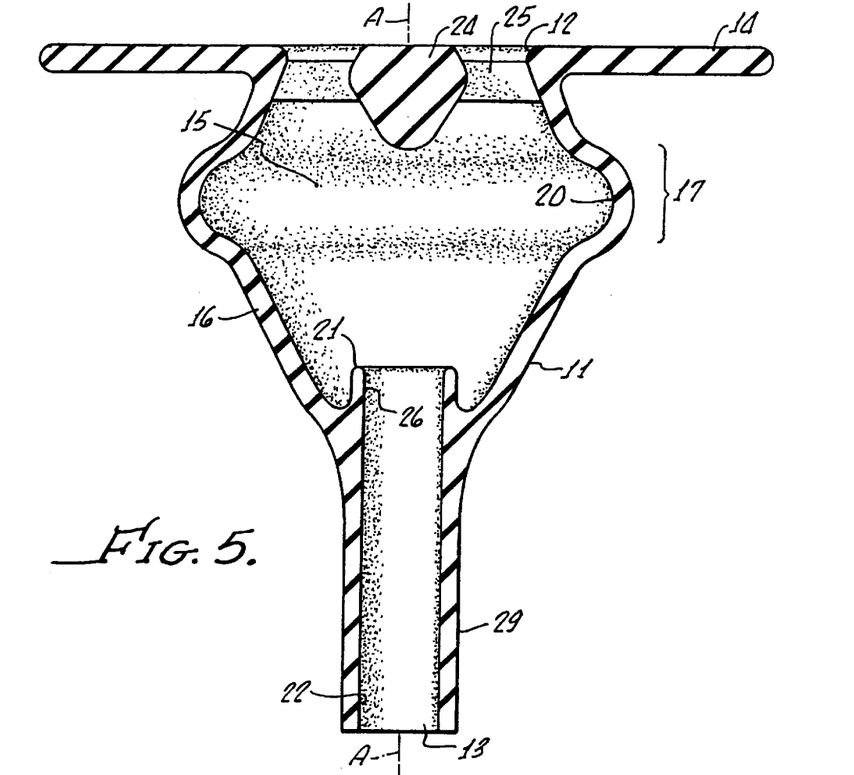
FIG. 5 is a view in cross section of the alternate valve as would be seen along line 5—5 of FIG. 4.
Figure 8:
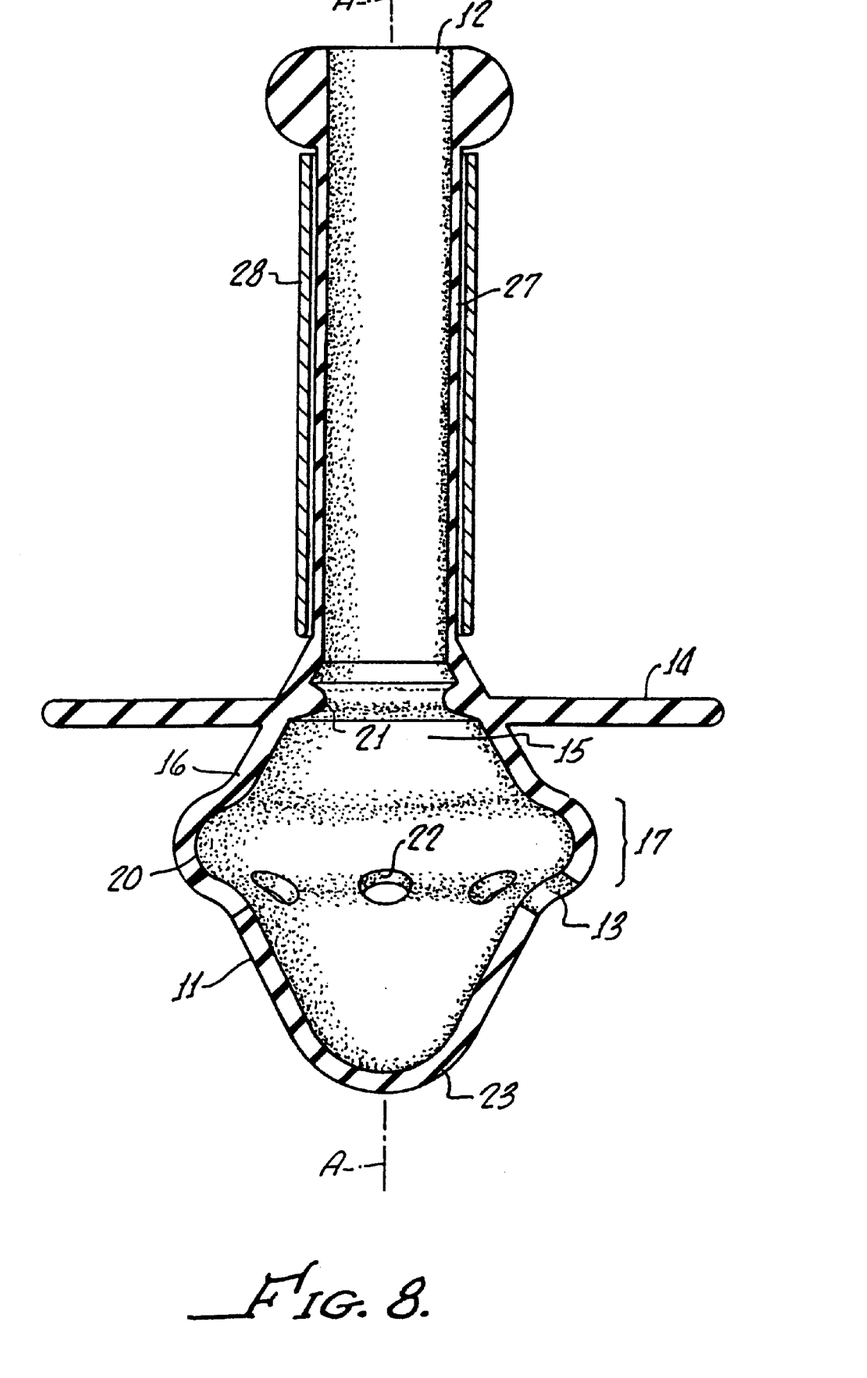
FIG. 8 is a view in cross section of the alternative valve as would be seen along line 8—8 of FIG. 7.
Figure 9:
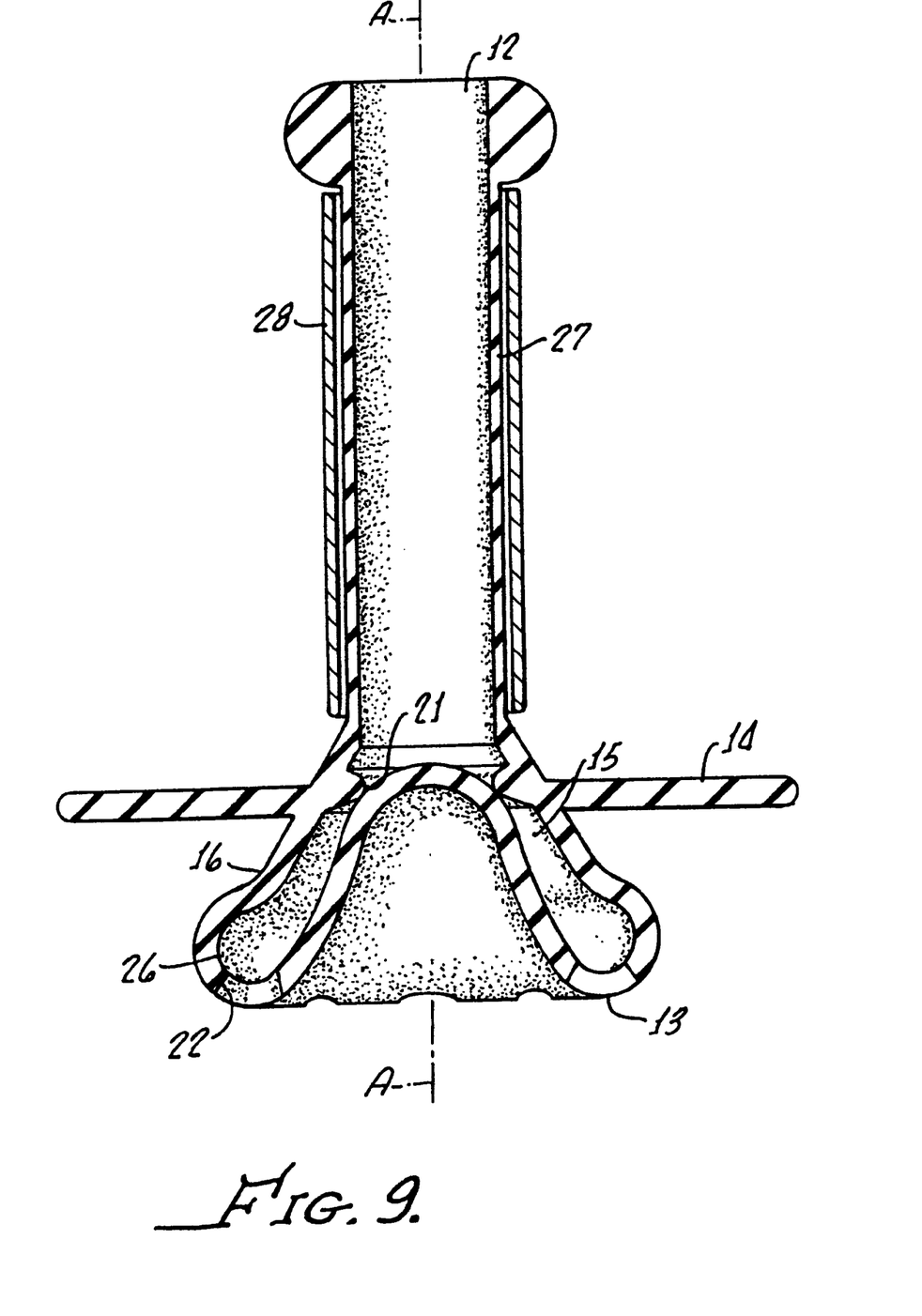
FIG. 9 is a view in cross section of the alternative valve similar to that of FIG. 8 but wherein therein the alternative valve is shown flipped over center with respect to the hinge in its alternative valve closed position.

A passage 15 is formed within and passes through the bulbous tube 11 for extending from the inlet 12 along an axis A—A therethrough between the inlet 12 and outlet 13. A wall 16, in FIGS. 3, 5, 6 and 8, of the bulbous tube 11 is preferably integral therewith. The wall 16 is in the preferred embodiment located between the inlet 12 and the outlet 13. Consistent with the configuration of the bulbous tube 11 the wall 16 is about 0.5 mm and has a barrel shape 17 as shown in FIGS. 2, 5 and 8. The barrel shape 17 tapers toward the inlet 12 and the outlet 13 so the bulbous tube 11 is wider therebetween. Similarly, the passage 15 through the bulbous tube 11 is wider between the inlet 12 and the outlet 13. The wall 16 is between an inside 18 and an outside 19 as seen the view in cross section of FIGS. 3, 5, 6 and 8. The preferred wall 16 is about 0.5 mm thick but the particular thickness is more a function of the durometer of the flexible polymer. The preferred polymer is C-Flex TPE Thermoplastic made by Consolidated Polymer Technologies, Inc. of Largo, Fla. C-Flex polymer has an 18 shore A durometer and the preferred wall 16 thickness of 0.5 mm; the valve 10 seating force is 15 grams and the over center force is about 50 grams. Of course the forces are a balance between the force to hold the valve 10 closed and the adhesive connection about the body orifice.

A hinge 20 is an integral part of the wall 16 and runs about the bulbous tube 11. The hinge 20 is preferred to be located axially in the wall 16 substantially wherein the barrel shape 17 wall 16 defines the passage 15 therethrough; that is at the widest part of the bulbous tube 11. The hinge 20 acts as an area of preferential bending at the barrel shape 17 so the bulbous tube 11 is either normally barrel shaped 17, in FIGS. 1, 2, 4, 5, 7 and 8, or flipped with the outlet 13 thereof folded about the hinge 20 and into the passage 15 in FIGS. 3 and 6.

The force to flip the hinge 20 has been measured in the range of about 10 to 100 grams but preferably 15 grams as explained. While the preferred hinge 20 is, that is either open or closed, the hinge 20 can also be arranged to be normally closed such that to keep it open the outlet 13 must be pulled away from a seat 21 by the user or the pressure of urination force from the bladder down the urethra may be applied for holding the outlet 13 away from the seat 21. This form of hinge 20 operation can be considered monostable but the valve 10 would look the same since the bias of the hinge 20 is not really apparent in illustrations. Consequently, as used herein the term, "bistable" includes normally open or closed valves 10 or alternatively normally closed valves 10 as explained.

Seat 21 is positioned within the bulbous tube 11 on the inside 18 of the wall 16. The seat 21 is be disposed within the passage 15 to engage the outlet 13 when the bulbous tube 11 is flipped into the passage 15 after bending the hinge 20 acutely. The outlet 13 is then moved along the axis A—A toward the inlet 12 so the outlet 13 is held against the seat 21 to seal the inlet 12 and close the passage 15. The seat 21 is axially between the inlet 12 and the wide part of the barrel shape 17 of the bulbous tube 11, see FIGS. 2, 5 and 8.

One or more holes 22 are preferably dispose through the wall 22. Each hole 22 might be located in a plane substantially normal to the axis and away from the inlet 12 and axially beyond the hinge 20. In one preferred alternative the outlet 13 may surround a bottom 23 of the bulbous tube 11 so that when flipped bulbous tube 11 moves the bottom 23 axially into the passage 15. The bottom 23 in FIGS. 1, 2 and 3 locates the one or more holes 22 dispose through the wall 16 in contact with the seat 21 and positions the bottom 23 to close the inlet 12; this is best shown in the view in cross section of FIGS. 1, 2, 4, 5, 7 and 8.

Figure 4:
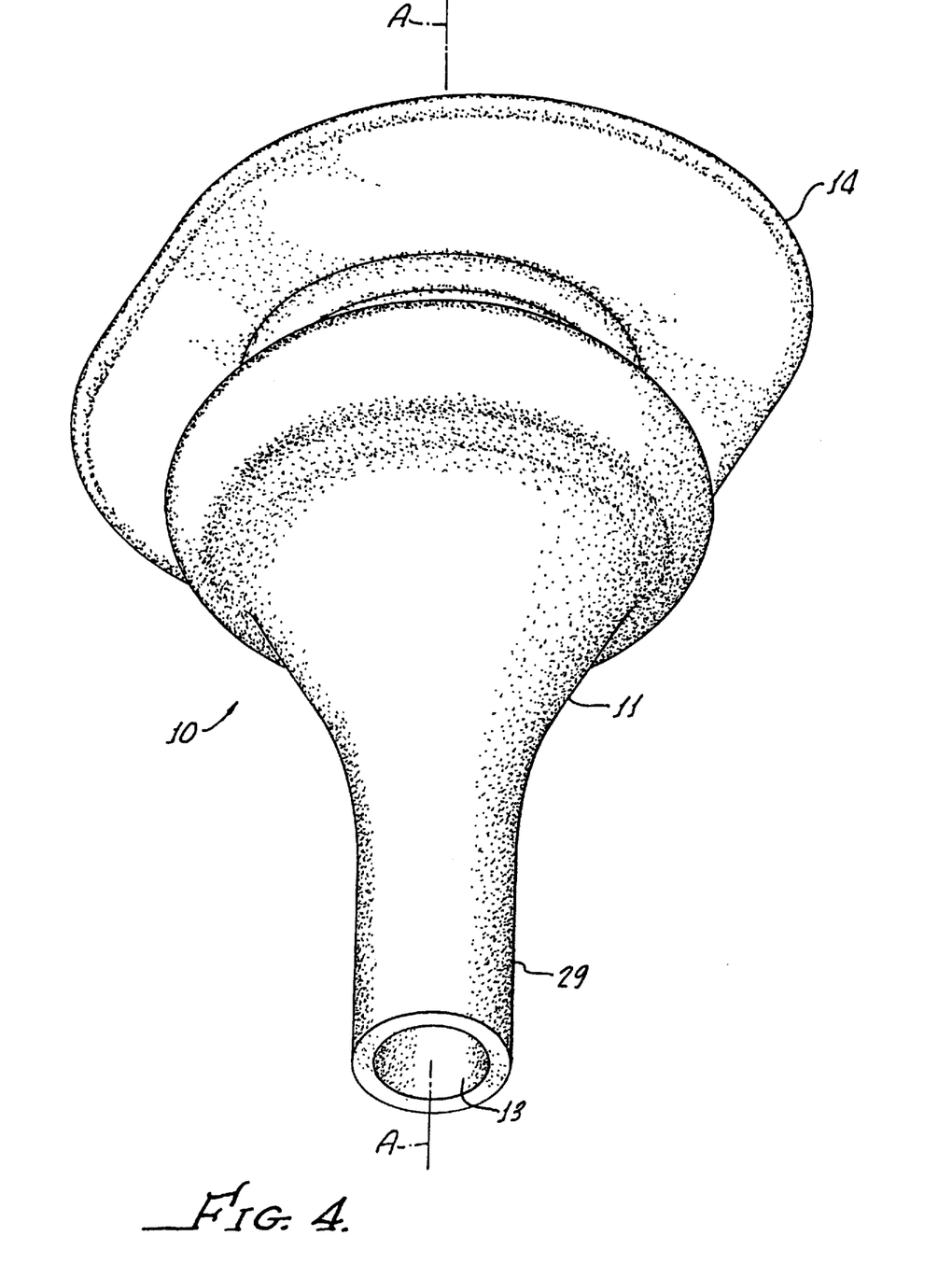
FIG. 4 is a view in perspective of an alternate valve adapted for closing a body orifice (not shown) wherein the alternate valve is shown in its open position.
Figure 6:
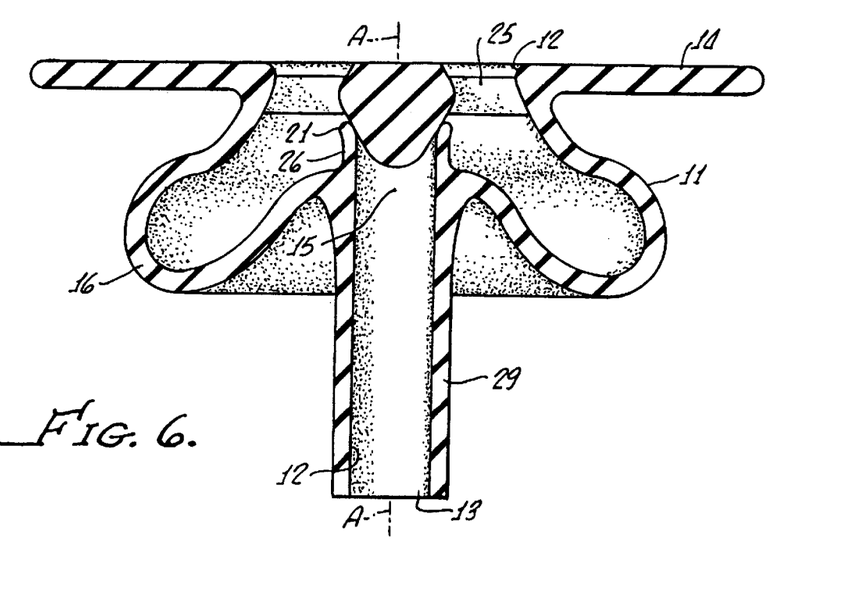
FIG. 6 is a view in cross section of the alternate valve similar to that of FIG. 5 but wherein therein the alternate valve is shown flipped over center with respect to the hinge in its alternate valve closed position.
Figure 7:
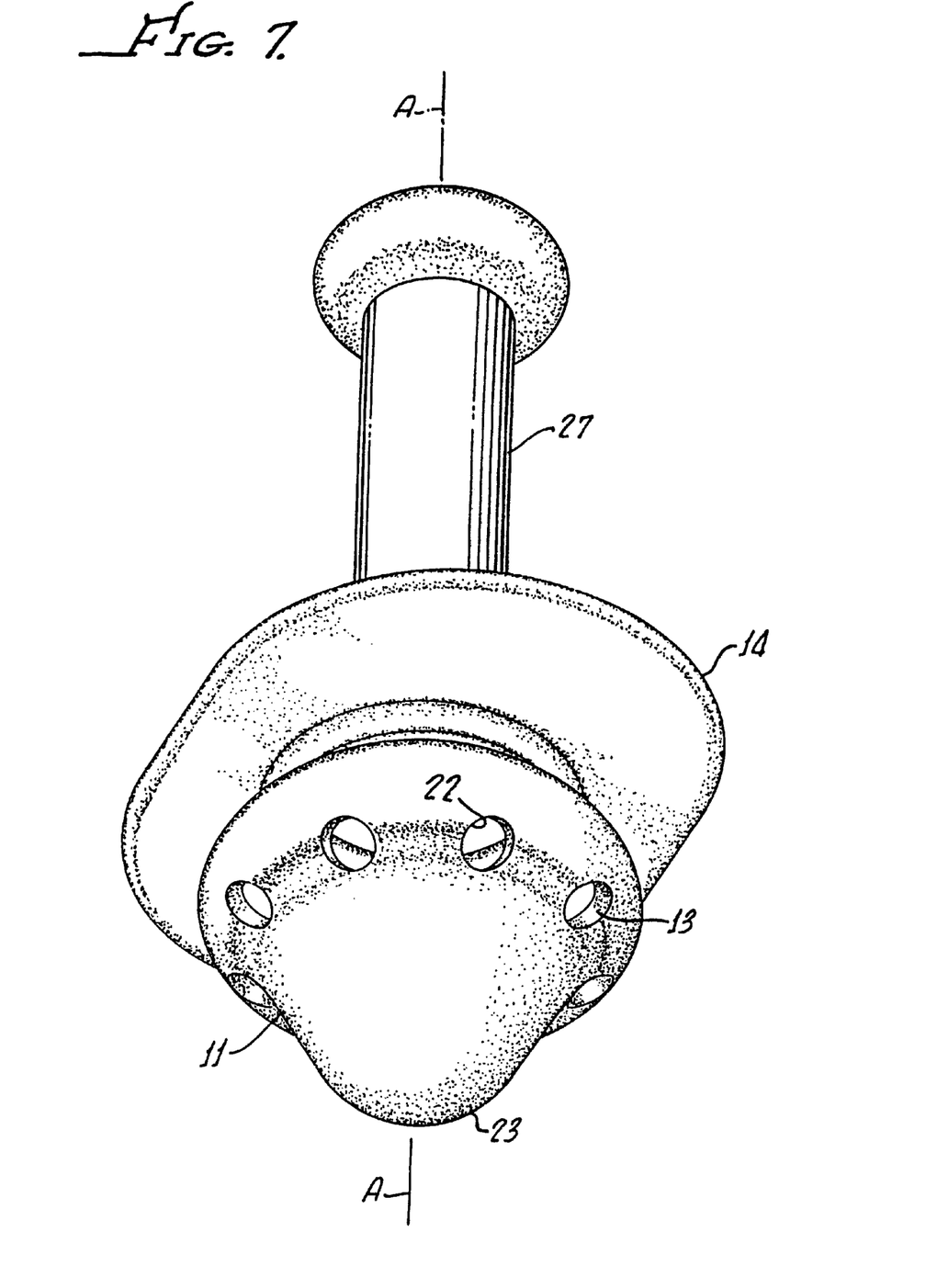
FIG. 7 is a view in perspective of an alternative valve adapted for closing a body orifice (not shown) wherein the alternate valve is shown in its open position.

The outlet 13 in another alternate embodiment of FIGS. 4, 5 and 6 includes a plug 24 supported from the wall 16 and within the outlet 13 by a web 25 so that when the flipped bulbous tube 11 moves the plug 24 axially through the passage 15 the plug 24 seats; this is best shown in the view in cross section of FIGS. 5 and 6. In that alternate configuration the plug 24 contacts the seat 21 and closes the inlet 12. The wall 16 about the inlet 12 may in this version include a pipe 26 depending at the wall 16 inside 18 thereabout. The pipe 26 in FIGS. 5 and 6 is thus in the passage 15 so the seat 21 is most preferably on the pipe 26 away from the inlet 12. Consequently, the seat 21 and the pipe 26 can be adapted to engage remotely, or axially along the passage 15, closing the inlet 12.

Similarly in another alternative, the inlet 12 might include a duct 27 positioned thereabout to surround the inlet 12 and extend passage 15 away from the outlet 13. The duct 27, the flange 14 and the bulbous tube 11 are thus in that arrangement adapted for fluid communication with the body orifice. The duct 27 extends into the urethra (not shown) may have a gel 28 in FIG. 8 about it to protect the patient's body, help the fit therein and ease insertion.

The bulbous tube 11 is preferred to be circular in cross section as shown in all the Figures and substantially symmetrical about the axis A—A as shown in the preferred valves 10. The preferred inlet 12 and outlet 13 are substantially normal to the axis A—A but need not be symmetric or circular. The bulbous tube 11 is formed of a flexible polymer by molding. The outlet 13 may have a grip 29 in FIGS. 2, 3, 4, 5 and 6 projecting therefrom for use in pulling the outlet 13 to flip the hinge 20 and open the passage 15 between the inlet 12 and outlet 13.

A method of making valve 10 adapted for closing an orifice includes steps. Forming bulbous tube 11 of a flexible material is a step. The step of having on the bulbous tube 11 inlet 12 fixed for placement across the orifice and outlet 13 positioned away from the orifice is a step. The step of locating flange 14 with a generally flat ring shape around the inlet 12 of the bulbous tube 11 to interface about the orifice is performed in this method. Extending passage 15 within and through the bulbous tube 11 from the inlet 12 along axis A—A therethrough is a step. Having barrel shaped 17 wall 16 on the bulbous tube 11 with the wall 16 tapering toward the inlet 12 and the outlet 13 and thus wider therebetween is a step. Locating the wall 16 between inside 18 and outside 19 is a step.

Locating hinge 20 about the bulbous tube 11 and in the wall 16 as an area of preferential bending so the bulbous tube 11 is either normally barrel shaped 17 or flipped with the outlet 13 folded about the hinge 20 into the passage 15 is a step. Preferentially bending the hinge 20 is a step. The step of locating seat 21 on the inside 18 of the wall 16 to engage the outlet 13 when the bulbous tube 11 is flipped into the passage 15 by bending the hinge 20 acutely so the outlet 13 is moved along the axis A—A toward the inlet 12 and held against the seat 21 is in the method.

A method of using the valve 10 has the bulbous tube 11 formed of a flexible material. The bulbous tube 11 has the inlet 12 fixed across the orifice and outlet 13 opposite thereto. The bulbous tube 11 has barrel shape 17 tapering toward the inlet 12 and the outlet 13 so the hinge 20 is about the bulbous tube 11. The hinge 20 is an area of preferential bending. The bulbous tube 11 is either normally barrel shaped 17 or flipped with the outlet 13 folded about the hinge 20 so seat 21 within the bulbous tube 11 seals the outlet 13. The method of using with the step of flipping the bulbous tube 11 by bending the hinge 20 acutely moves the outlet 13 toward the inlet 12 for holding against the seat 21. The method of using with the step of unfolding the acutely bent hinge 20 by acutely bending hinge 20 by pressurizing the seat 21 at the inlet 12 but within the bulbous tube 11 to unseal the outlet 13 or by pressing about the hinge 20 to flip the outlet 13 away from the seat 21.

While several embodiments have been shown and described, the valve 10 sought to be protected by the claims that follow has the outlet 13 that seats or is unrestricted excepted when seated.

What is claimed is:

1. A valve adapted to close a body orifice, the valve comprising:

a proximal portion having surfaces defining an inlet adapted to be placed across the body orifice, a flange projecting from the proximal portion adapted to associate the valve with the body orifice;

a bulbous distal portion spaced distally from said proximal portion; the bulbous distal portion having valve closing surfaces;

surfaces defining an outlet situated distally from the inlet, inner surfaces defining a passage extending from the inlet to the outlet;

abutment surfaces that are sized and shaped to complement the valve closing surfaces, a hinge affording movement of the bulbous distal portion between i) an open position with the valve closing surfaces spaced from the abutment surfaces to afford flow of fluid from the inlet through the outlet, ii) and a closed position with the valve closing surfaces engaging the abutment surfaces and closing at least a portion of the passage to resist flow of fluid out the outlet; and the valve being constructed so that a) the valve closing surfaces are inherently biased against the abutment surfaces when the bulbous distal portion is in the closed position, and b) the bulbuous distal portion is capable of remaining stable in the open position.

2. A valve according to claim 1 wherein the flange is situated substantially adjacent the inlet, the valve is adapted to restrict flow of urine from a urethra of a patient, and the valve is adapted to be associated with the urethra without any structure projecting into the urethra.

3. A valve according to claim 1 wherein the hinge is barrel shaped.

4. A valve according to claim 1 wherein the outlet includes at least two holes.

5. A valve according to claim 1 further including a grip situated on the bulbous distal portion, the grip being sized and shaped to be grasped and pulled so that, when the valve is in the closed position, pulling on the grip can overcome the inherent bias of the hinge to move the valve to the open position.

6. A valve according to claim 1 wherein the abutment surfaces comprise a seat.

7. A valve according to claim 1 wherein the abutment surfaces and valve closing surfaces comprise a plug and a seat.

8. A valve according to claim 1 wherein the hinge is constructed to afford manual flipping of the distal portion from the open toward the closed position by manually pressing on the bulbous distal portion.

9. A valve adapted to restrict the flow of urine through a urethra of a patient, the valve comprising:
   a proximal portion having surfaces defining an inlet adapted to be associated with the urethra,
   a projection extending from the proximal portion adapted to associate the valve with the patient;
   a distal portion spaced distally from said proximal portion; the distal portion having sealing surfaces;
   surfaces defining an outlet spaced from the inlet;
   surfaces defining a passage within the valve from the inlet to the outlet;
   a seat that is sized and shaped to complement the sealing surfaces,
   a hinge affording movement of the distal portion between i) an open position with the sealing surfaces spaced from the seat to afford flow of urine from the inlet through the outlet, ii) and a closed position with the sealing surfaces engaging the seat and closing at least a portion of the passage to resist flow of urine out the outlet;
   biasing means for biasing the sealing surfaces against the seat when the distal portion is in the closed position,
   the valve being constructed so that the distal portion is capable of remaining stable in the open position, and
   a grip situated on the distal portion, the grip being sized and shaped to be grasped and pulled so that, when the valve is in the closed position, pulling on the grip can overcome the biasing means to move the valve to the open position.

10. A valve according to claim 9 wherein the biasing means comprises constructing the valve from a flexible polymer and constructing the hinge to be barrel shaped.

11. A valve according to claim 9 wherein the projection is situated substantially adjacent the proximal portion.

12. A valve according to claim 11 wherein the projection has a biocompatible adhesive adhered thereto that is adapted to adhere the projection to a patient to associate the valve with a patient without any structure of the valve projecting into the urethra of the patient.

13. A method of making a valve adapted to close an orifice, the method including the steps of:
   forming a bulbous distal portion having a sealing surface; and a proximal portion having surfaces forming an inlet adapted to be placed across the orifice,
   forming a flange that projects from the proximal portion;
   locating a seat within the proximal portion, the seat having surfaces for engaging the sealing surface of the distal portion,
   forming an outlet capable of being positioned away from the proximal portion;
   extending a passage from the inlet to the outlet;
   forming a barrel shaped wall that tapers toward the inlet and the outlet;
   forming a hinge in the wall to afford bending between i) an open position with the valve sealing surface spaced from the seat to afford flow of fluid from the inlet through the outlet, ii) and a closed position with the valve sealing surface engaging the seat and closing at least a portion of the passage to resist flow of fluid out the outlet.

14. A method according to claim 13 further including forming a grip on the bulbous distal portion.

15. A method according to claim 13 including the step of integrally molding the valve from a flexible, biocompatible polymer.

16. A method of using a valve including a proximal portion having surfaces defining an inlet; a projection extending from the proximal portion, a distal portion spaced from said proximal portion; the distal portion having sealing surfaces; surfaces defining an outlet spaced from the inlet; surfaces defining a passage within the valve from the inlet to the outlet; a seat that is sized and shaped to complement the sealing surfaces, a hinge affording movement of the distal portion between i) an open position with the sealing surfaces spaced from the seat to afford flow of fluid from the inlet through the outlet, ii) and a closed position with the sealing surfaces engaging the seat to resist flow of fluid out the outlet; and biasing means for biasing the sealing surfaces against the seat when the distal portion is in the closed position, the valve being constructed so that the distal portion is capable of remaining stable in the open position, the method of using a valve comprising the steps of:
   associating the valve with a body orifice using the projection, and
   moving the distal portion of the valve to the closed position to resist flow of fluids from the body orifice by pressing on the distal portion to flip the distal portion by bending the hinge.

17. A method according to claim 16 wherein the distal portion of the valve has a grip and the method includes the step of:
   pulling on the grip against the bias of the biasing means to move the distal portion from the closed toward the open position.

* * * * *